(12) United States Patent
Vyas et al.

(10) Patent No.: US 10,738,192 B2
(45) Date of Patent: Aug. 11, 2020

(54) PROCESS FOR THE PREPARATION OF INDIGO CARMINE

(71) Applicant: DISHMAN CARBOGEN AMCIS LIMITED, Navrangpura, Ahmedabad (IN)

(72) Inventors: Janmejay Rajnikant Vyas, Ahmedabad (IN); Himani Dhotre, Ahmedabad (IN); Narasimha Sarma, Ahmedabad (IN); Dilip N. Patel, Ahmedabad (IN); Piyush Sangani, Ahmedabad (IN); Arpan Kiritbhai Shah, Ahmedabad (IN); Babulal R. Patel, Ahmedabad (IN); Devang Wadia, Ahmedabad (IN)

(73) Assignee: DISHMAN CARBOGEN AMCIS LIMITED, Navrangpura, Ahmedabad (IN)

(*) Notice: Subject to any disclaimer, the term of this patent is extended or adjusted under 35 U.S.C. 154(b) by 0 days.

(21) Appl. No.: 15/780,545

(22) PCT Filed: Nov. 25, 2016

(86) PCT No.: PCT/IB2016/057126
§ 371 (c)(1),
(2) Date: May 31, 2018

(87) PCT Pub. No.: WO2017/093866
PCT Pub. Date: Jun. 8, 2017

(65) Prior Publication Data
US 2018/0346727 A1    Dec. 6, 2018

(30) Foreign Application Priority Data

Dec. 1, 2015   (IN) .......................... 4535/MUM/2015

(51) Int. Cl.
| | | |
|---|---|---|
| *C09B 67/00* | (2006.01) | |
| *C09B 61/00* | (2006.01) | |
| *C09B 69/00* | (2006.01) | |
| *C07D 209/36* | (2006.01) | |
| *C09B 7/02* | (2006.01) | |
| *C09B 67/54* | (2006.01) | |
| *C09B 67/48* | (2006.01) | |
| *B01J 27/20* | (2006.01) | |

(52) U.S. Cl.
CPC ................. *C09B 7/02* (2013.01); *B01J 27/20* (2013.01); *C07D 209/36* (2013.01); *C09B 61/00* (2013.01); *C09B 67/00* (2013.01); *C09B 67/0025* (2013.01); *C09B 67/0096* (2013.01); *C09B 69/00* (2013.01); *B01J 2219/00058* (2013.01); *B01J 2523/68* (2013.01)

(58) Field of Classification Search
CPC .......... C09B 61/00; C09B 67/00; C09B 69/00
See application file for complete search history.

(56) References Cited

U.S. PATENT DOCUMENTS

| | | |
|---|---|---|
| 4,370,424 A | 1/1983 | Baumann |
| 2014/0152748 A1 | 6/2014 | Toosi |

OTHER PUBLICATIONS

PubChem CID 3705 {National Center for Biotechnology Information. PubChem Database. Indigotindisulfonic acid, CID=3705, https://pubchem.ncbi.nlm.nih.gov/compound/Indigotindisulfonic-acid (accessed on Jun. 10, 2019), create date Mar. 25, 2005 (Year: 2005).*
Yamamoto et al., Bulletin of the Chemical Society of Japan, vol. 84, No. 1, 2011, pp. 82-89. (Year: 2011).*
Das, P.J. and Baruah, A. "Oxidative Degradation of Indole Using Mixed Ligand Co(II) Complex and Hydrogen Peroxide : Selective Formation of Indole Dimers" (2011) Chemistry and Biology Interface 1(3): 355-359.
Substance Record for SID 798260 (2004) PubChem Open Chemistry Database (https://pubchem.ncbi.nlm.nih.gov/substance/798260#section=Top).

* cited by examiner

Primary Examiner — Laura L Stockton
(74) Attorney, Agent, or Firm — Volpe and Koenig, P.C.

(57) ABSTRACT

The present invention relates to an improved process for preparation of Indigo carmine of Formula (I), in high purity, more than 99.5%.

20 Claims, 2 Drawing Sheets

PROCESS FOR THE PREPARATION OF INDIGO CARMINE

CROSS REFERENCE TO RELATED APPLICATION

This application is a 35 USC § 371 national stage of PCT/IB2016/057126, which was filed Nov. 25, 2016 and claimed priority to IN 4535/MUM/2015, filed Dec. 1, 2015.

FIELD OF INVENTION

The present invention provides a novel process for the preparation of Indigo carmine having high purity 99.90%.

BACKGROUND OF THE INVENTION

Indigo carmine, chemically known as 3,3'-dioxo-2,2'-bis-indolyden-5,5'-disulfonic acid disodium salt, commonly used as a pH indicator, often in a 0.2% aqueous solution. It is blue at pH 11.4 and yellow at 13.0. Indigo carmine is also a redox indicator, turning yellow upon reduction. Another use is as a dissolved ozone indicator through the conversion to isatin-5-sulfonic acid. This reaction has been shown not to be specific to ozone, however: it also detects superoxide, an important distinction in cell physiology. It is also used as a dye in the manufacturing of capsules.

In obstetric surgery, indigo carmine solutions are sometimes employed to detect amniotic fluid leaks. In urologic surgery, intravenous injection of indigo carmine is often used to highlight portions of the urinary tract. The dye is filtered rapidly by the kidneys from the blood, and colors the urine blue. This enables structures of the urinary tract to be seen in the surgical field, and demonstrate if there is a leak. However, the dye can cause a potentially dangerous increase in blood pressure in some cases.

Indigo Carmine is excreted largely by the kidneys, retaining its blue color during passage through the body. Elimination of the dye begins soon after injection, appearing in the urine within 10 minutes in average cases. The biological half-life is 4 to 5 minutes following intravenous injection. Larger quantities are necessary when intramuscular injection is employed. Appearance time and elimination are delayed following intramuscular injection.

As described FDA indications of indigo carmine: Originally employed as a kidney function test, the chief application of Indigo Carmine at present is localizing ureteral orifices during cystoscopy and ureteral catheterization Dye and pigments 6, page-135-154(1985) describes process for making trisulpho, disulpho, mono sulpho Indigo. In accordance with the journal, Indigo can prepared by reacting sulphuric acid as well as 30% fuming sulphuric acid, here they disclosed the disulphonic indigo will preparation temperature at 100° C. but not describe process or any analytical data forming disulphonic salt of indigo. In this journal process Indigo carmine compound is not isolating or not easy filtration, also Indigo carmine not getting having purity as per the ICH guideline.

Bull. Chem. Soc. Jap. Vol. 84, no. 1, page-82-89(2011), intermediate of Indigo, process describe using Molybledenumhexacarbonyl as catalyst, in presence of acid as acetic acid or phenyl acetic acid or additive, oxidizing agent cumene hydroperoxide (CHP) in cumene (82%) solution using alcohol, in this publication large amount of catalyst (0.05 mol) and large amount of solvent using.

U.S. Pat. No. 1,427,863 describe process for preparing indigo (isatina-anilid) using thioaminde, sulphuric acid, ammoniumsulphite, water.

U.S. Pat. No. 1,588,960 describe process for making indigo using aniline oxidizing in acid solution to produce chromophore blue treated with organic acid to give indigo.

GB181673 describe process for preparing indigo using mineral oil, sodamide, sodium salt of phenyl glycine/hydroxyethyl aniline and mixture of caustic soda and caustic potash.

OBJECTIVE OF THE INVENTION

The main objective of the present invention is to provide an improved process for the preparation of Indigo carmine having grater than 99.5%.

Yet another objective of the present invention is to provide an improved process, which having high purity grater than 99.0% indigotindisulfonic acid of intermediate compound formula (IV).

Yet another objective of the present invention is to provide a simple and environmentally friendly process for the preparation of Indigo carmine, which avoids use of hazardous and expensive reagents.

Yet another objective of the present invention is to provide a process with a good yield and high purity grater than 99.5%.

Yet another objective of the present invention is to provide an improved process for Indigo carmine, which is simple and industrially applicable.

SUMMARY OF INVENTION

The present invention relates to a novel improved process for the preparation of Indigo carmine of Formula (I) having grater than 99.5%.

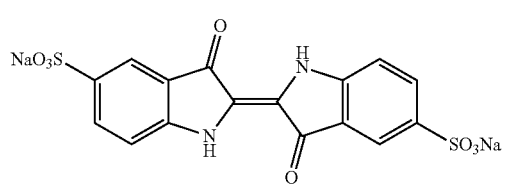

I which comprises:

a) Indole of compound formula (II)

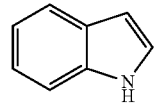

II treating with hydrogenperoxide in presence of catalyst in alcoholic solvent to give indigo of compound formula (III)

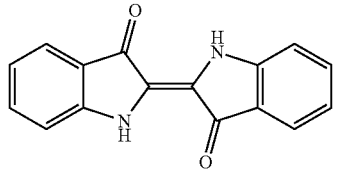
III b) Indigo of compound formula (III)

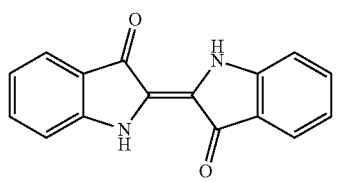
III react with sulfuric acid and adding organic solvent then wash or purification in ester solvent to given to indigodisulfonic acid of compound formula (IV).

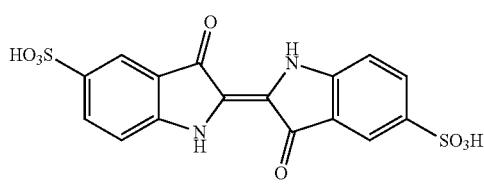
IV c) reacting indigodisulfonic acid of Formula (IV)

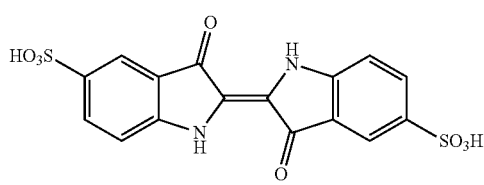
IV using aqueous media in sodium source of compound and wash with ketonic solvent to give title compound formula (I).

DETAILED DESCRIPTION OF THE INVENTION

A first object of the present invention to provide an improved process for the preparation of Indigo carmine of Formula (I) having grater than 99.5%,

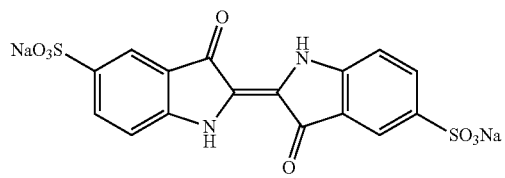
I

Thus, condensation indigodisulfonic acid of compound formula (IV)

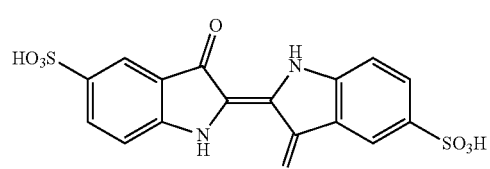
IV using aqueous media in sodium source of compound and wash with ketonic solvent to give title compound formula (I).

Another embodiment of present invention process carried out in aqueous media as water, and sodium source, here sodium source define as sodium metal, sodium hydroxide, sodium acetate, but preferably salt is sodium hydroxide.

Another embodiment of the present invention reaction is carried out at temperature range about 15° C. to 40° C., but preferably temperature is 25° C. to 30° C.

Another embodiment of invention is product wash with in ketonic solvent and nitrile as solvent, ketonic and nitrile solvent define as acetone, Acetonitrile but preferably solvent is acetone.

The crude compound purification reaction is usually run in a suitable nitrile and ketonic solvent such as water or a mixture of water and a ketonic and nitrile solvent such as acetone, Acetonitrile but preferably solvent is acetone and water.

Present invention provides isolation of compound formula (IV)

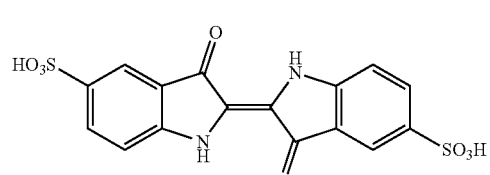
IV

Another embodiment of the present invention making compound formula (IV) having HPLC purity achieved 99.0%.

Figure 1:
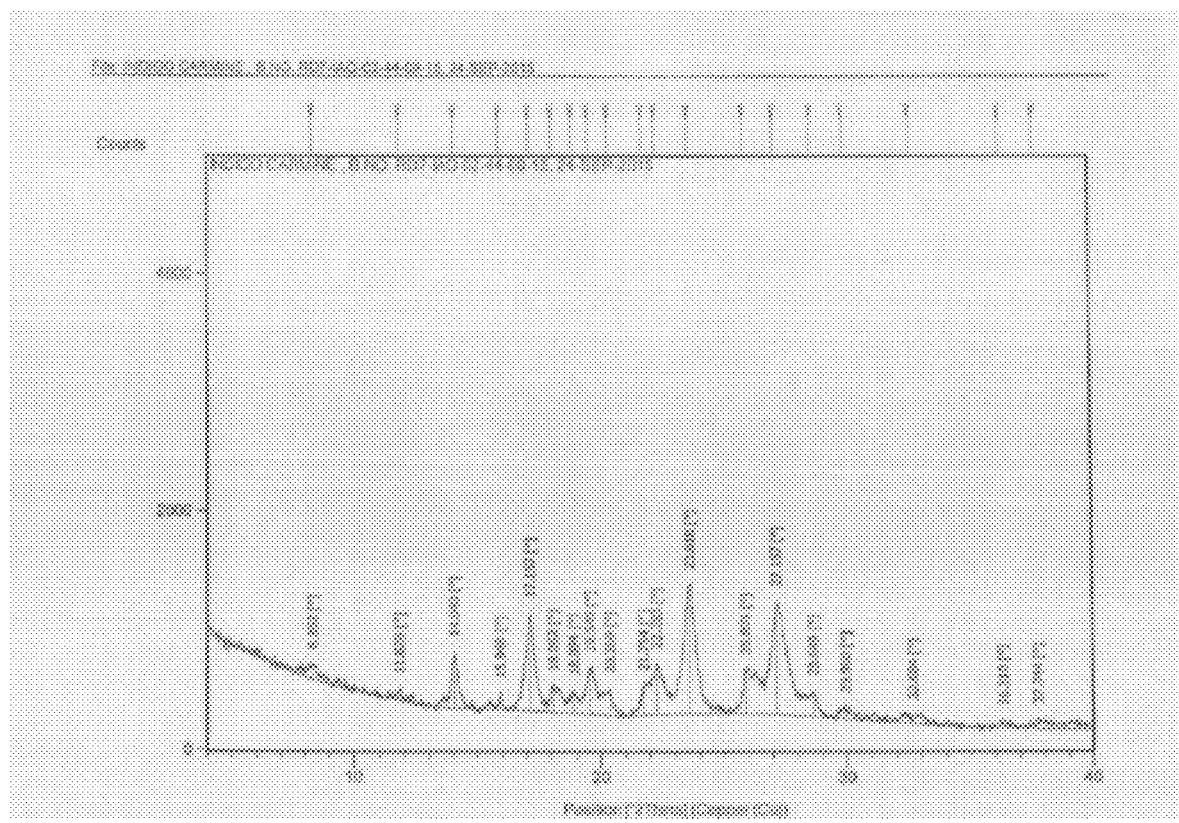
FIG. 1: A crystalline form of Indigodisulfonic acid of formula (IV) having obtain by example 2.

A crystalline form of Indigodisulfonic acid of Formula (IV) characterized by X-ray powder diffraction (XRPD) pattern having peaks at ° 2 theta value 14.04, 17.15, 23.61 and 27.15±2° C., FIG. 1: XRPD pattern of powder diffractogram of Indigodisulfonic acid of Formula (IV)

Figure 2:
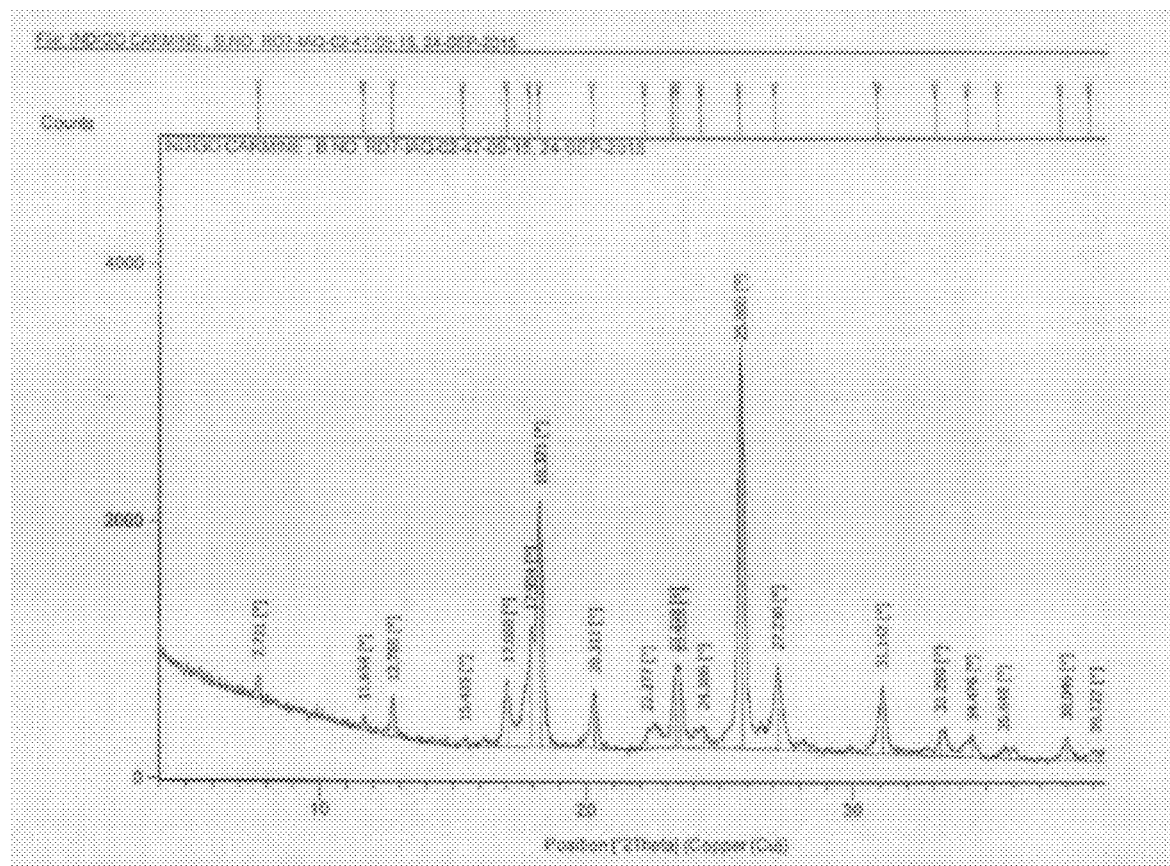
FIG. 2: A crystalline form of Indigodisulfonic acid of formula (IV) having obtain by example 3.

A crystalline form of Indigodisulfonic acid of Formula (IV) characterized by X-ray powder diffraction (XRPD) pattern having peaks at ° 2 theta value 12.76, 17.08, 17.95, 18.32, 20.31, 25.86 and 27.23±2° C., FIG. 2: XRPD pattern of powder diffractogram of Indigodisulfonic acid of Formula (IV)

Process for making indigodisulfonic acid of compound formula (IV) comprising Indole of compound formula (II)

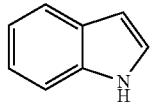

treating with peroxide in presence of catalyst in alcoholic solvent to give indigo of compound formula (III)

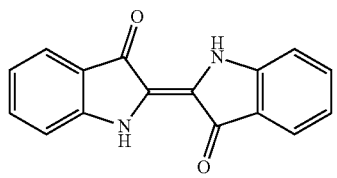

Indigo of compound formula (III)

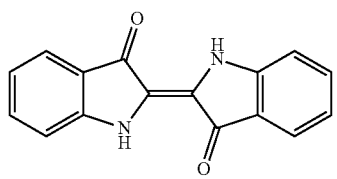

react with sulfuric acid and adding organic solvent then wash or purification in ester solvent to given to indigodisulfonic acid of compound formula (IV).

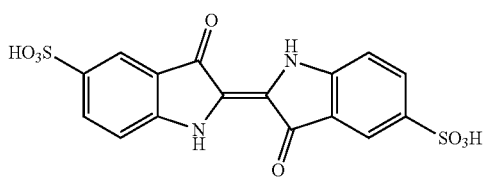

Another embodiment of invention making indigo of compound formula (III) is reaction carried out in alcoholic solvent, solvent define as methanol, ethanol, isopropanol, n-butanol, tert-butanol but preferably solvent is tert-butanol.

Another embodiment of invention making indigo of compound formula (III) is reaction carried out in peroxide, the reaction carried out in peroxide compound is define as hydrogen peroxide, cumene hydrogen peroxide in cumene preferably cumene hydrogen peroxide in cumene.

Another embodiment of invention making indigo of compound formula (III) is reaction carried out in presence of catalyst is call Molybledenumhexacarbonyl $Mo(CO)_6$. Catalyst using less amount of 0.00085 mole.

Another embodiment of the present invention making indigo of compound formula (III) reaction is carried out at temperature range about 75° C. to 120° C., but preferably temperature is 80° C. to 85° C.

Another embodiment of the present invention process according to step-(b) using the compound formula (V)

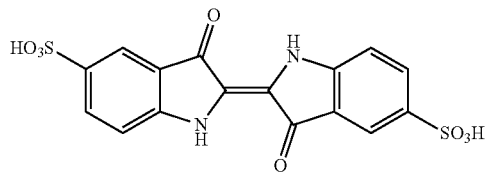

Indigo of compound formula (III)

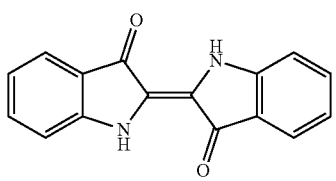

react with sulfuric acid and adding organic solvent then wash or purification in ester solvent to given to indigodisulfonic acid of compound formula (IV).

Another embodiment of the present invention making compound formula (IV) reaction is carried out in organic acid, acetic acid, isopropyl acetate but preferable acetic acid.

Another embodiment of invention making compound formula (IV) is wash/purification carried out in ester solvent, solvent define as ethyl acetate, isopropyl acetate but preferably solvent is ethyl acetate.

Another embodiment of the present invention reaction is carried out at temperature range about 75° C. to 90° C., but preferably temperature is 80° C. to 85° C.

Another embodiment of the present invention purification is carried out at temperature range about 70° C. to 90° C., but preferably temperature is 75° C. to 85° C.

Throughout the description and claims the word "comprise" and variations of the word are not intended to exclude other technical features, additives, components, or steps. The content of the abstract of the present application is incorporated herein as reference. Additional objects, advantages and features of the invention will become apparent to those skilled in the art upon examination of the description or may be learned by practice of the invention. The following examples are provided by way of illustration, and is not intended to be limiting of the present invention.

Example—1

Preparation of Indigo from Indole

Indole (100 gm, 0.85 mole) was suspended in tert-Butanol (750 ml, 7.5 vol) and add Acetic acid (5.07 gm, 0.08 mole), Molybledenumhexacarbonyl (80%) (340.6 gm, 1.79 mole). Heat and maintain for 7 hrs at temperature 80-86° C. Cool the reaction mass. Filter material and wash with Methanol to yield the title compound as solid.

Yield: 75 gm

Example—2

Preparation of Indigo Disulfonic Acid Compound from Indigo

Add concentrated Sulfuric acid (380 gm, 3.8 mole) and heat to 95-105° C. Charge Indigo (100 gm, 0.38 mole) and maintain at 95-105° C. for 2 hrs. Immediate cool to room temperature and suspended in Acetic acid (1500 ml, 15 vol) at temperature 20-25° C. Stir and filter. Wash with acetic acid (100 ml, 1 vol) and Ethyl acetate (800 ml, 8 vol). Further hot slurry with Ethyl acetate (450 ml, 4.5 vol) to yield the title compound as solid.

Yield: 145 gm (Solid)

Chromatographic Purity (by HPLC): ≥90 (% area),

Example—3

Preparation of Indigo Disulfonic Acid Compound from Indigo

Add concentrated Sulfuric acid (380 gm, 3.8 mole) and heat to 95-105° C. Charge Indigo (100 gm, 0.38 mole) and maintain at 95-105° C. for 2 hrs. Immediate cool to room temperature and suspended in Acetone (5 L, 50 vol) at temperature 0-10° C. and add Ethyl acetate (5 L, 50 vol). Stir and filter. Wash with Acetone:Ethyl acetate (1:1) to yield the title compound as solid.

Yield: 145 gm (Solid)

Chromatographic Purity (by HPLC): ≥90 (% area),

Example—4

Preparation of Indigotindisulfonate Sodium

Indigo disulfonic acid compound (100 gm, 0.24 mole) was dissolved in water (400 ml, 4 vol) and adjusted pH 6.5 to 9 by using sodium hydroxide (19 gm, 0.48 mole) solution in water (300 ml, 3 vol). Add Acetone (500 ml, 5 vol) and stir. Filter and wash with Acetone to yield the title compound as solid.

Yield: 90 gm (Solid)

Chromatographic Purity (by HPLC): ≥97 (% area),

Example—5

Purification of Indigotindisulfonate Sodium

Indigotindisulfonate sodium (100 gm, 0.21 mole) was suspended in water (2000 ml, 20 vol). Heat to 95-100° C. and stir for 30 min at temperature 95-100° C. Cool to 55-60° C. and add Acetone (1000 ml, 10 vol). Cool to 25-30° C. Stir for 1 hr at temperature 25-30° C. Filter and wash with Acetone: water (1:1) mixture to yield the title compound as solid.

Yield: 75 gm (Solid)

Chromatographic Purity (by HPLC): ≥99.5 (% area)

The invention claimed is:

1. An improved process for the preparation of Indigo carmine of formula (I) having a purity of 99.5%,

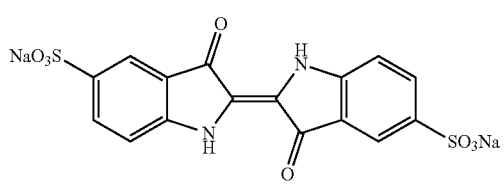

the process comprising:

a) treating an Indole of compound formula (II)

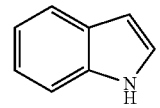

with peroxide in the presence of a catalyst in an alcoholic solvent to give an indigo of compound formula (III)

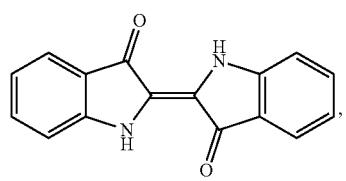

b) reacting the Indigo of compound formula (III)

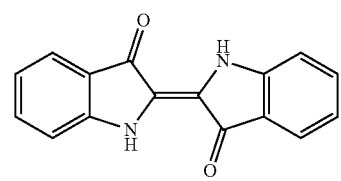

with sulfuric acid and adding an organic solvent then washing or purifying in an ester solvent to produce an indigodisulfonic acid of compound formula (IV)

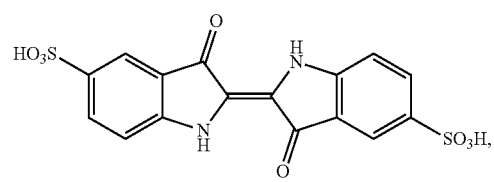

and c) reacting indigodisulfonic acid of formula (IV)

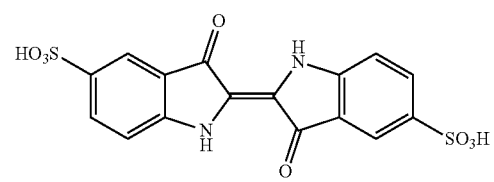

in an aqueous media with a sodium source compound and washing with a nitrile or a ketonic solvent to give the Indigo carmine of formula (I).

2. The process according to claim 1, wherein in step (a) the reaction carried is out in an alcohol solvent selected from group methanol, ethanol, isopropanol, n-butanol, and tert-butanol.

3. The process according to claim 1, wherein in step (a) the reaction is carried out in a peroxide compound selected from hydrogen peroxide and cumene hydrogen peroxide in cumene.

4. The process according to claim 1, wherein in step (a) the reaction is carried out at a temperature ranging from 80° C. to 120° C.

5. The process according to claim 1, wherein in step (a) the reaction is carried out in the presence of a catalyst, which is Molybledenumhexacarbonyl ($Mo(CO)_6$).

6. The process according to claim 1, wherein in step (b) the reaction is carried out at a temperature ranging from 50° C. to 90° C.

7. The process according to claim 1, wherein in step (b) the reaction is carried out in a solvent, which is an organic solvent.

8. The process according to claim 1, wherein in step (b) the washing or purifying is carried out in the ester solvent, which is selected from methyl acetate and ethyl acetate.

9. The process according to claim 1, wherein the aqueous media is only water.

10. The process according to claim 1, wherein in step (c) the reaction is carried out at a temperature ranging from 20° C. to 40° C.

11. The process according to claim 1, wherein in step (c) the sodium source compound is selected from sodium metal, sodium hydride, and sodium hydroxide.

12. The process according to claim 11, wherein in step (c) the washing is carried out in a solvent selected from acetone and acetonitrile.

13. The process according to claim 2, wherein in step (a) the alcohol solvent is tert-butanol.

14. The process according to claim 3, wherein in step (a) the reaction is carried out in cumene hydrogen peroxide in cumene.

15. The process according to claim 4, wherein in step (a) the reaction is carried out at a temperature ranging from 95° C. to 100° C.

16. The process according to claim 6, wherein in step (b) the reaction is carried out at a temperature ranging from 75° C. to 85° C.

17. The process according to claim 7, wherein in step (b) the reaction is carried out in acetic acid.

18. The process according to claim 8, wherein in step (b) the ester solvent is ethyl acetate.

19. The process according to claim 10, wherein in step the reaction is carried out at a temperature ranging from 25° C. to 30° C.

20. The process according to claim 12, wherein in step the washing is carried out in acetone.

* * * * *